United States Patent [19]

Brooks et al.

[11] Patent Number: 5,032,588
[45] Date of Patent: Jul. 16, 1991

[54] THIAZOLE LIPOXYGENASE-INHIBITING COMPOUNDS DERIVED FROM NON-STEROIDAL ANTIINFLAMMATORY CARBOXYLIC ACIDS

[75] Inventors: Dee W. Brooks, Libertyville; Francis A. J. Kerdesky, Grayslake, both of Ill.

[73] Assignee: Abbott Laboratories, Abbott Park, Ill.

[21] Appl. No.: 447,756

[22] Filed: Dec. 8, 1989

[51] Int. Cl.$^5$ .................. C07D 417/04; C07D 279/22; A61K 31/54; A61K 31/425

[52] U.S. Cl. .................. 514/224.8; 514/256; 514/342; 514/367; 514/369; 544/38; 544/331; 546/144; 546/167; 546/280; 548/105; 548/110; 548/179; 548/182; 548/186; 548/187

[58] Field of Search ............... 548/182, 110, 179, 182, 548/186, 187; 544/38, 331; 514/224.8, 342, 367, 369, 256

[56] References Cited

U.S. PATENT DOCUMENTS

| | | | |
|---|---|---|---|
| 4,393,075 | 7/1983 | Terao et al. | 514/519 |
| 4,608,390 | 8/1986 | Summers, Jr. | 514/575 |
| 4,623,661 | 11/1986 | Summers, Jr. | 514/575 |

OTHER PUBLICATIONS

Nelson, Chem. Abst. 101-130499j (1984).
Irikura et al., Chem. Abst. 103-87870a (1985).
Corey et al., J.A.C.S., 1984, 106, 1503-1504.
Foye et al., Chem. Abst. 69-1553u (1968).
Ota, Chem. Abst. 73-77241u (1970).

*Primary Examiner*—Cecilia Shen
*Attorney, Agent, or Firm*—Jerry F. Janssen; Andreas M. Danckers; Steven F. Weinstock

[57] ABSTRACT

Compounds of the formulae:

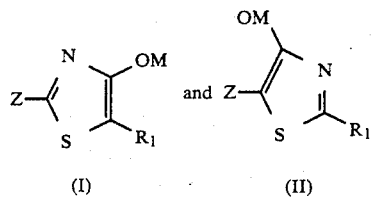

and pharmaceutically acceptable salts, esters and pro-drugs thereof, wherein M and $R_1$ are independently selected from among optionally substituted alkyl, alkenyl, cycloalkyl, cycloalkenyl, aryl, arylalkyl, arylalkenyl, reduced heteroaryl and reduced heteroarylalkyl groups, and Z is the residue of a compound selected from the class of compounds known as non-steroidal antiinflammatory grugs containing a carboxylic acid group, of the general form Z-COOH.

8 Claims, No Drawings

THIAZOLE LIPOXYGENASE-INHIBITING COMPOUNDS DERIVED FROM NON-STEROIDAL ANTIINFLAMMATORY CARBOXYLIC ACIDS

TECHNICAL FIELD

This invention relates to inhibitors of lipoxygenase enzymes, and more particularly to novel lipoxygenase-inhibiting thiazole compounds which are derived from non steroidal antiinflammatory drugs (NSAID) containing the carboxylic acid functionality. It also relates to methods and compositions for inhibiting lipoxygenase enzymes in humans and animal hosts in need of such treatment.

BACKGROUND OF THE INVENTION

5-Lipoxygenase is the first enzyme in the pathway leading to the biosynthesis of leukotrienes (LTs). In the course of this pathway or "cascade", arachidonic acid, the 5-lipoxygenase substrate from which leukotriene (LT) products are derived, is first converted to 5-hydroperoxy-eicosatetraenoic acid (5-HPETE) and subsequently reduced to 5-hydroxyeicosatetraenoic acid (5-HETE) or converted to $LTA_4$. The reactive leukotriene intermediate $LTA_4$ is enzymatically hydrated to $LTB_4$ or conjugated to the tripeptide glutathione to produce $LTC_4$. $LTA_4$ can also be hydrolyzed nonenzymatically to form two isomers of $LTB_4$. Successive proteolytic cleavage steps convert $LTC_4$ to $LTD_4$ and $LTE_4$. Other products resulting from further oxygenation steps have also been described. (See Serhan, C. N., Hamberg, M., and Samuelsson, B., Lipoxins: Novel Series of Biologically Active Compounds Formed from Arachidonic Acid in Human Leukocytes, *Proceedings of the National Academy of Sciences, USA*, 81:5335 (1985)).

Products of the 5-lipoxygenase cascade are extremely potent substances which produce a wide variety of biological effects, often in the nanomolar to picomolar concentration range. (Sirois, P., "Pharmacology of the Leukotrienes", Advances in Lipid Research, R. Paoletti & D. Kritchevesky, eds., Academic Press, 21:79 (1985).) The remarkable potencies and diversity of actions of products of the 5-lipoxygenase pathway have led to the suggestion that they play important roles in a variety of diseases. The presence of LTs $A_4$–$E_4$ has been associated with a number of disease states, including asthma, allergic rhinitis, rheumatoid arthritis, gout, psoriasis, inflammatory disorders of the skin, acne, atherosclerosis, adult respiratory distress syndrome, inflammatory bowel disease, endotoxin shock, ischemia induced myocardial injury, and central nervous pathophysiology.

The enzyme 5-lipoxygenase catalyzes the first step leading to the biosynthesis of all the leukotrienes, and inhibition of this enzyme is therefore likely to limit the effects of these potent mediators of numerous pathophysiological processes. Agents which block or modulate the activity of lipoxygenase enzymes thus represent a promising class of therapeutic agents for use in the treatment of diseases involving leukotriene pathogenesis. (Brooks, D. W., Bell, R. L., and Carter, G. W., Chapter 8: Pulmonary and Antiallergy Agents, *Annual Reports in Medicinal Chemistry*, Allen, R. C., ed., Academic Press (1988)). Examples of 5-lipoxygenase inhibitors known to the art are: AA-861, disclosed in U.S. Pat. No. 4,393,075, issued July 12, 1983 to Terro et al.; pyrazolopyridines, disclosed in the European Patent Application of Iriburn et al., Ser. No. 121,806, published Oct. 17, 1984; arachidonyl hydroxamic acid, disclosed in Corey et al., *J. Am. Chem. Soc.*, 106:1503 (1984) and in the European Patent Application of Nelson, Ser. No. 104,468, published Apr. 4, 1984; BW-755C, disclosed in Radmark et al., *FEBS Letters*, 110:213 (1980); nordihydroguaiaretic acid, disclosed in Marris et al., *Prostaglandins*, 19:371 (1980); Rev-5901, disclosed in Coutts, Meeting Abstract 70, *Prostaglandins and Leukotrienes* '84; benzoxaprofen, disclosed in Walker, *Pharm. Pharmacol.*, 31:778 (1979); and hydroxamic acids, disclosed in U.S. Pat. Nos. 4,608,390 and 4,623,661, issued Aug. 16 and Nov. 18, 1986, respectively.

SUMMARY OF THE INVENTION

The present invention comprises compounds which exhibit unexpected activity as inhibitors of lipoxygenase enzymes, particularly 5-lipoxygenase, and thereby reduce the biosynthesis of leukotrienes $LTB_4$, $LTC_4$, $LTD_4$ and $LTE_4$. Also disclosed is a method of inhibiting 5- and/or 12-lipoxygenase activity in a mammal in need of such treatment by administering to such a mammal the inventive compounds in an amount effective to inhibit lipoxygenase activity.

One aspect of the present invention is the group of compounds having the formulae:

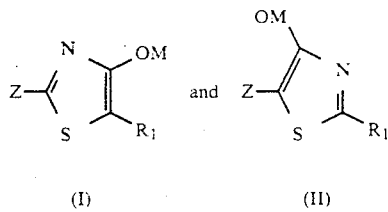

(I)        (II)

and pharmaceutically acceptable salts, esters and prodrugs thereof.

In these compounds $R_1$ is selected from the group consisting of alkyl, alkenyl, cycloalkyl, cycloalkenyl, aryl, arylalkyl, arylalkenyl, reduced heteroaryl, reduced heteroarylalkyl, and substituted derivatives thereof. Substituents may be independently chosen from the group consisting of halogen, alkyl, halosubstituted alkyl, aryl, arylalkyl, reduced heteroaryl, arylalkoxy, cyano, nitro, $-SO_2R_4$, $-C(O)R_4$, $-NR_5R_6$, $-OR_6$, $-C(O)CX_1X_2NR_6R_7$, $-C(O)N(OH)R_6$, $-NR_6C(O)R_4$, $-CR_5(NH_2)CO_2R_5$, $-NHCX_1X_2CO_2R_5$, $-N(OH)C(O)NR_5R_6$, $-N(OH)C(O)R_4$, $-NHC(O)NR_5R_6$, $-C(NOH)NHOH$, and $-C(O)NHNR_5R_6$.

$R_4$ is independently selected at each occurrance from the group consisting of hydrogen, alkyl, alkenyl, cycloalkyl, cycloalkenyl, aryl, arylalkyl, reduced heteroaryl, reduced heteroarylalkyl, $-OR_5$, an amino residue of formula $-NHCX_1X_2CO_2R_5$, and $-NR_6R_7$.

$R_5$ is independently selected at each occurrance from the group consisting of hydrogen, alkyl, alkenyl, cycloalkyl, aryl, arylalkyl, reduced heteroaryl, and reduced heteroarylalkyl.

$R_6$ and $R_7$ are independently selected at each occurrance from the group consisting of hydrogen, alkyl, alkenyl, cycloalkyl, aryl, arylalkyl, reduced heteroaryl, reduced heteroarylalkyl, and $-(CH_2)_nOP_5$ wherein n is 2 to 4.

$X_1$ and $X_2$ are independently selected at each occurrance from the group consisting of hydrogen, alkyl, alkenyl, cycloalkyl, aryl, and arylalkyl.

M is selected from the group consisting of hydrogen, a pharmaceutically acceptable salt, $-C(O)R_4$, $-C(O)CX_1X_2NR_6R_7$, $-CR_8R_9OR_{10}$, $-CH_2CR_8(OR_{10})CH_2OR_{11}$, and $-SiR_{12}R_{13}R_{14}$.

$R_8$, $R_9$, $R_{10}$ and $R_{11}$ are independently selected at each occurrance from the group consisting of hydrogen, alkyl, aryl, arylalkyl, and $-(CH_2)_nOR_5$ wherein n is 2 to 4. Alternatively, at least two of $R_8$, $R_9$, $R_{10}$ and $R_{11}$ together can form a carbocyclic or heterocyclic or reduced heterocyclic ring system containing 5-10 atoms.

$R_{12}$, $R_{13}$ and $R_{14}$ are independently selected at each occurrance from the group consisting of alkyl and aryl.

Z is the residue of a compound selected from the class of compounds known as non steroidal antiinflammatory drugs containing a carboxylic acid group, of the general form Z—COOH.

Another aspect of the present invention is the group of compositions comprising a pharmaceutically acceptable carrier and a therapeutically effective amount of one of the above inventive compounds.

Yet another aspect of the invention is a method for treating asthma, allergic rhinitis, rheumatoid arthritis, gout, psoriasis, acne, atherosclerosis, adult respiratory distress syndrome, inflammatory bowel disease, endotoxin shock, ischemia-induced myocardial injury, or central nervous pathophysiology in a mammal in need of such treatment.

DETAILED DESCRIPTION OF THE INVENTION

The novel compounds of this invention are those of Formula I and Formula II:

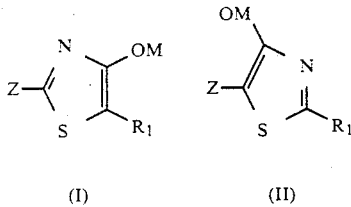

(I)    (II)

and pharmaceutically acceptable salts, esters and prodrugs thereof.

$R_1$ is selected from the group consisting of alkyl, alkenyl, cycloalkyl, cycloalkenyl, aryl, arylalkyl, arylalkenyl, reduced heteroaryl, reduced heteroarylalkyl, and substituted derivatives thereof with one or more substituents independently chosen from the group consisting of halogen, alkyl, halosubstituted alkyl, aryl, arylalkyl, reduced heteroaryl, arylalkoxy, cyano, nitro, $-SO_2R_4$, $-C(O)R_4$, $-NR_5R_6$, $-OR_6$, $-C(O)CX_1X_2NR_6R_7$, $-C(O)N(OH)R_6$, $-NR_6C(O)R_4$, $-CR_5(NH_2)CO_2R_5$, $-NHCX_1X_2CO_2R_5$, $-N(OH)C(O)NR_5R_6$, $-N(OH)C(O)R_4$, $-NHC(O)NR_5R_6$, $-C(NOH)NHOH$, and $-C(O)NHNR_5R_6$.

$R_4$ is selected at each occurrence from the group consisting of hydrogen, alkyl, alkenyl, cycloalkyl, cycloalkenyl, aryl, arylalkyl, reduced heteroaryl, reduced heteroarylalkyl, $-OR_5$, an amino residue of formula $-NHCX_1X_2CO_2R_5$, and $-NR_6R_7$.

$R_5$ is selected at each occurrence from the group consisting of hydrogen, alkyl, alkenyl, cycloalkyl, aryl, arylalkyl, reduced heteroaryl, and reduced heteroarylalkyl.

$R_6$ and $R_7$ are independently selected at each occurrance from the group consisting of hydrogen, alkyl, alkenyl, cycloalkyl, aryl, arylalkyl, reduced heteroaryl, reduced heteroarylalkyl, and $-(CH_2)_nOR_5$ wherein n is 2 to 4.

$X_1$ and $X_2$ are independently selected at each occurrance from the group consisting of hydrogen, alkyl, alkenyl, cycloalkyl, aryl, and arylalkyl.

M is selected from the group consisting of hydrogen, a pharmaceutically acceptable salt, $-C(O)R_4$, $-C(O)CX_1X_2NR_6R_7$, $-CR_8R_9OR_{10}$, $-CH_2CR_8(OR_{10})CH_2OR_{11}$, and $-SiR_{12}R_{13}R_{14}$.

$R_8$, $R_9$, $R_{10}$ and $R_{11}$ are independently selected at each occurrance from the group consisting of hydrogen, alkyl, aryl, arylalkyl, and $-(CH_2)_nOR_5$ wherein n is 2 to 4. Alternatively, at least two of $R_8$, $R_9$, $R_{10}$ and $R_{11}$ together can form a carbocyclic or heterocyclic or reduced heterocyclic ring system containing 5-10 atoms.

$R_{12}$, $R_{13}$ and $R_{14}$ are independently selected at each occurrance from the group consisting of alkyl and aryl.

Z is the residue of a compound selected from the class of compounds known as non-steroidal antiinflammatory drugs containing a carboxylic acid group, of the general form Z—COOH.

Compounds considered within the classification of non-steroidal antiinflammatory drugs (NSAID) have been documented by J. Lombardino in "Nonsteroidal Antiinflammatory Drugs", Wiley-Interscience, New York, 1985. Examples of compounds of this class of antiinflammatory drugs include but are not limited to the following:

(1) benoxaprofen,
(2) benzofenac,
(3) bucloxic acid,
(4) butibufen,
(5) carprofen,
(6) cicloprofen,
(7) cinmetacin,
(8) clidanac,
(9) clopirac,
(10) diclofenac,
(11) etodolac,
(12) fenbufen,
(13) fenclofenac,
(14) fenclorac,
(15) fenoprofen,
(16) fentiazac,
(17) flunoxaprofen,
(18) furaprofen,
(19) furobufen,
(20) furofenac,
(21) ibuprofen,
(22) ibufenac,
(23) indomethacin,
(24) indoprofen,
(25) isoxepac,
(26) ketoprofen,
(27) lonazolac,
(28) metiazinic,
(29) miroprofen,
(30) naproxen,
(31) oxaprozin,
(32) oxepinac,
(33) pirprofen,
(34) pirazolac,

(35) protizinic acid,
(36) sulindac,
(37) suprofen,
(38) tiaprofenic acid,
(39) tolmetin, and
(40) zomepirac.

Examples of compounds which are themselves within the scope of the present invention and/or can be used according to the methods of the present invention include, but are not limited to, the following:

2-[1-(6-methoxy-2-naphthyl)ethyl]-5-phenyl-4-hydroxythiazole,
2-[1-(4-isobutylphenyl)ethyl]-5-phenyl-4-hydroxythiazole,
2-[(4-isobutylphenyl)methyl]-5-phenyl-4-hydroxythiazole,
2-[1-(4-isobutylphenyl)propyl]-5-phenyl-4-hydroxythiazole,
5-[1-(6-methoxy-2-naphthyl)ethyl]-2-phenyl-4-hydroxythiazole,
2-[1-(6-methoxy-2-naphthyl)ethyl]-5-(4-methoxyphenyl)-4-hydroxythiazole,
2-[1-(6-methoxy 2-naphthyl)ethyl]-5-(4-carbomethoxyphenyl)-4-hydroxythiazole,
2-[1-(4-isobutylphenyl)propyl]-5-(4-methoxyphenyl)-4-hydroxythiazole,
2-[1-(4-isobutylphenyl)propyl]-5-(4-methoxycarbonylphenyl)-4-hydroxythiazole,
2-[1-(4-isobutylphenyl)propyl]-5-(4-fluorophenyl)-4-hydroxythiazole,
2-[1-(4-isobutylphenyl)propyl]-5-(2,4-difluorophenyl)-4-hydroxythiazole,
2-[1-(4-isobutylphenyl)propyl]-5-(propyl)-4-hydroxythiazole,
2-[1-(4-isobutylphenyl)propyl]-5-(1-ethylphenyl)-4-hydroxythiazole,
2-[1-(4-isobutylphenyl)propyl]-5-(1-ethenylphenyl)-4-hydroxythiazole,
2-[1-(4-isobutylphenyl)propyl]-5-cyclohexyl-4-hydroxythiazole,
2-[1-(4-isobutylphenyl)propyl]-5-cyclopropyl-4-hydroxythiazole,
2-[1-(4-isobutylphenyl)propyl]-5-(thien-2-yl)-4-hydroxythiazole,
2-[1-(4-isobutylphenyl)propyl]-5-(methylthien-2-yl)-4-hydroxythiazole,
2-[1-(4-isobutylphenyl)propyl]-5-[3-(ethoxycarbonyl)propyl]-4-hydroxythiazole,
2-[1-(4-isobutylphenyl)propyl]-5-(4-N-methyl-N-hydroxyamidobutyl)-4-hydroxythiazole,
2-[1-(4-isobutylphenyl)propyl]-5-(4-hydroxybutyl)-4-hydroxythiazole,
2-[1-(4-isobutylphenyl)propyl]-5-(4-phenyl)-4-acetylthiazole,
2-[1-(4-isobutylphenyl)propyl]-5-(4-phenyl)-4-hydroxythiazole potassium salt,
2-[1-(4-isobutylphenyl)propyl]-5-(4-phenyl)-4-trimethylsilyloxythiazole,
2-[1-(4-isobutylphenyl)propyl]-5-(4-phenyl)-4-glycinylthiazole,
2-[1-(4-isobutylphenyl)propyl]-5-(4-phenyl)-4-succinylthiazole,
2-[1-(4-isobutylphenyl)propyl]-5-(4-phenyl)-4-succinyl-N-methyl-N-hydroxyamidothiazole,
5-[1-(6-methoxy-2-naphthyl)ethyl]-2-(4-fluorophenyl-4-hydroxythiazole,
5-[1-(6-methoxy-2-naphthyl)ethyl]-2-(2,4-difluorophenyl-4-hydroxythiazole,
5-[1-(6-methoxy-2-naphthyl)ethyl]-2-(4-methoxyphenyl-4-hydroxythiazole,
5-[1-(6-methoxy-2-naphthyl)ethyl]-2-(thien-3-yl)-4-hydroxythiazole,
5-[1-(6-methoxy-2-naphthyl)ethyl]-2-(4-pyridyl)-4-hydroxythiazole,
5-[1-(6-methoxy-2-naphthyl)ethyl]-2-(2-pyridyl)-4-hydroxythiazole,
5-[1-(6-methoxy-2-naphthyl)ethyl]-2-(2-benzothienyl)-4-hydroxythiazole,
5-[1-(6-methoxy-2-naphthyl)ethyl]-2-(2-benzothiazoyl)-4-hydroxythiazole,
5-[1-(6-methoxy-2-naphthyl)ethyl]-2-(2-thiazoyl)-4-hydroxythiazole,
5-[1-(6-methoxy-2-naphthyl)ethyl]-2-phenyl-4-acetoxythiazole,
5-[1-(6-methoxy-2-naphthyl)ethyl]-2-phenyl-4-hydroxythiazole potassium salt,
5-[1-(6-methoxy-2-naphthyl)ethyl]-2-phenyl-4-methoxycarbonyloxythiazole,
5-[1-(6-methoxy-2-naphthyl)ethyl]-2-phenyl-4-N-methyl-N-hydroxycarbonyl-oxythiazole,
5-[1-(6-methoxy-2-naphthyl)ethyl]-2-phenyl-4-succinylthiazole,
5-[1-(6-methoxy-2-naphthyl)ethyl]-2-[1-(4-isobutylphenyl)ethyl]-4-acetoxythiazole,
5-[1-(6-methoxy-2-naphthyl)ethyl]-2-[1-(4-isobutylphenyl)propyl]-4-hydroxythiazole,
2-[1-(4-isobutylphenyl)ethyl]-5-[1-(4-isobutylphenyl)ethyl]-4-hydroxythiazole,
2-[1-(6-methoxy-2-naphthyl)ethyl]-5-[1-(4-isobutylphenyl)ethyl]-4-hydroxythiazole,
2-[1-(6-methoxy-2-naphthyl)ethyl]-5-[1-(4-isobutylphenyl)ethyl]-4-benzoylthiazole,
2-[1-(4-phenoxyphenyl)ethyl]-5-phenyl-4-hydroxythiazole],
2-[1-(2-(4-chlorophenyl)benzoxaz-5-yl)ethyl]-5-phenyl-4-hydroxythiazole,
2-[2-(4,5-diphenyloxaz-2-yl)ethyl]-5-phenyl-4-hydroxythiazole,
2-[2-(N-methyl-9-methoxyphenothiazin-4-yl)ethyl]-5-phenyl-4-hydroxythiazole, and
2-[5-fluoro-2-methyl-(4-methylsulfinylbenzylidene)-inden-3-ylmethyl]-5-phenyl-4-hydroxythiazole.

Preferred compounds of the present invention include, but are not limited to, the following:

2-[1-(6-methoxy-2-naphthyl)ethyl]-5-phenyl-4-hydroxythiazole,
2-[1-(4-isobutylphenyl)ethyl]-5-phenyl-4-hydroxythiazole,
2-[(4-isobutylphenyl)methyl]-5-phenyl-4-hydroxythiazole,
2-[1-(4-isobutylphenyl)propyl]-5-phenyl-4-hydroxythiazole, and
5-[1-(6-methoxy-2-naphthyl)ethyl]-2-phenyl-4-hydroxythiazole.

The compounds of the present invention can also be prepared in the form of pharmaceutically acceptable salts, esters and other prodrugs. Derivative salts include relatively non-toxic inorganic or organic acid addition salts or alkaline earth metal salts of the inventive compounds, which can be prepared in situ during the final isolation and purification of the compounds or by separately reacting the free base with a suitable organic or inorganic acid. Where the compounds include a basic functionality such as an amine or alkylamine, representative salts include hydrochloride, sulfate, acetate, maleate, lauryl sulphate and the like. Where an acidic functionality is present, salts such as sodium, calcium, potassium and magnesium salts may be formed.

Pharmaceutically acceptable esters and other prodrugs of the inventive compounds can be prepared by methods known in the art, such as those described in "Design of Prodrugs", Bundgaard, H., ed., Elsevier, Amsterdam, pp. 1–92 (1985). These prodrugs, which are formed by the addition of a metabolically cleavable group to compounds bearing a hydroxyl or carboxyl functionality, are converted in vivo to the parent compound and may provide improved absorption and bioavailability. Examples of such esters include glycyl, lysyl, acetyl and succinyl derivatives, while other prodrugs may be formed by the addition, for example, of alkanoyl, aroyl, aminocarbonyl, alkylaminocarbonyl, alkoxycarbonyl and silyl groups.

The term "alkyl" as used herein refers to a straight or branched chain radical containing 1 to 6 carbon atoms including, but not limited to, methyl, ethyl, n-propyl, isopropyl, n-butyl, sec-butyl, isobutyl and tert-butyl.

The term "alkylene" as used herein refers to a straight or branched chain intervening radical containing 1 to 6 carbon atoms including, but not limited to, —$CH_2$—, —$CH(CH_3)$—, —$CH(C_2H_5)$—, —$CH(CH_3)CH_2$— and —$(CH_2)_3$—.

The term "alkenyl" as used herein refers to a straight or branched chain radical containing 2 to 6 carbon atoms and a carbon-carbon double bond including, but not limited to, 1-propenyl, 2-propenyl, 2-methyl-1-propenyl, 1-butenyl and 2-butenyl.

The term "alkenylene" as used herein refers to a straight or branched chain intervening radical containing 2 to 6 carbon atoms and a carbon-carbon double bond, including, but not limited to, —CH=CH—, —C($CH_3$)=CH—, —CH=CH—$CH_2$—, —CH=C($CH_3$)—$CH_2$— and —$CH_2$CH(CH=$CH_2$)$CH_2$—.

The term "cycloalkyl" as used herein refers to cyclic radicals of 3 to 8 carbons, including, but not limited to, cyclopropyl, cyclobutyl, cyclopentyl and cyclohexyl.

The terms "alkoxy" and "thioalkoxy" as used herein refer to —$OR_{15}$ and —$SR_{15}$, respectively, wherein $R_{15}$ is an alkyl group, including, but not limited to, methoxy, ethoxy, isopropoxy, n-butoxy, sec-butoxy, isobutoxy, tert-butoxy, methylthio, ethylthio, isopropylthio, n-butylthio and tert-butylthio.

The term "alkylamino" as used herein refers to —$NHR_{16}$ wherein $R_{16}$ is an alkyl group.

The term "dialkylamino" as used herein refers to —$NR_{17}R_{18}$ wherein $R_{17}$ and $R_{18}$ are the same or different alkyl groups.

The term "aminocarbonyl" as used herein refers to —$C(O)NH_2$.

The term "alkylaminocarbonyl" as used herein refers to —$C(O)NHR_{19}$ wherein $R_{19}$ is an alkyl group.

The term "dialkylaminocabonyl" as used herein refers to —$C(O)NR_{20}R_{21}$ wherein $R_{20}$ and $R_{21}$ are the same or different alkyl groups.

The term "alkoxycarbonyl" as used herein refers to —$C(O)OR_{22}$ wherein $R_{22}$ is an alkyl group.

The term "alkanoyl" as used herein refers to —$C(O)R_{23}$ wherein $R_{23}$ is hydrogen or an alkyl group including, but not limited to, formyl, acetyl, propionyl, butyryl, isobutyryl and pivaloyl.

The term "carbocyclic" as used herein refers to saturated cyclic groups of three to six carbon atoms including, but not limited to, cyclopentyl and cyclohexyl.

The term "heterocyclic" as used herein refers to an unsaturated single- and fused-ring group of three to twelve atoms containing one or more heteroatoms selected from N, O and S including, but not limited to, thienyl, furanyl, thiazolyl, pyridyl, pyrimidyl, oxazolyl, benzothienyl, benzofuranyl, benzothiazolyl, indolyl, quinolyl and isoquinolyl.

The term "reduced heterocyclic" as used herein refers to a partially or completely hydrated heterocyclic group including, but not limited to, dihydrothienyl, tetrahydrothienyl, dihydrofuranyl, tetrahydrofuranyl, dihydrothiazole, tetrahydrothiazole, dihydroindolyl, tetrahydroindolyl, dihydroquinolyl and tetrahydroquinolyl.

The term "aryl" as used herein refers to a substituted or unsubstituted carbocyclic aromatic radical including, but not limited to, phenyl, 1- or 2-naphthyl, and the like, and refers also to a substituted or unsubstituted heterocyclic aromatic group wherein the heterocyclic aromatic group is a 5- or 6-membered aromatic ring containing from one to three heteroatoms independently selected from oxygen, sulfur and nitrogen. The term "aryl" also includes bicyclic groups in which any of the above heterocyclic aromatic rings, including, but not limited to, furanyl, thienyl, pyridyl, indolyl, quinolyl and benzimidazolyl, is fused to a benzene ring. Substituted aryl groups can be substituted with one or two substituents independently selected from hydroxy, halo, alkoxy, thioalkoxy, alkyl, nitro, amino, alkylamino, dialkylamino, haloalkyl, cyano, carboxy, alkoxycarbonyl, aminocarbonyl, alkylaminocarbonyl and dialkylaminocarbonyl.

The term "reduced heteroaryl" as used herein refers to a partially or completely hydrated heteroatom-containing aryl group including, but not limited to, dihydrothienyl, tetrahydrothienyl, dihydrofuranyl, tetrahydrofuranyl, dihydropyridyl, tetrahydropyridyl, dihydroquinolyl, tetrahydroquinolyl, dihydroindolyl and tetrahydroindolyl.

The term "aroyl" as used herein refers to —$C(O)R_{24}$ wherein $R_{24}$ is an aryl group including, but not limited to, benzoyl, 1-naphthoyl, 2-naphthoyl and 2-furoyl.

The term "aryloxy" as used herein refers to —$OR_{25}$ wherein $R_{25}$ is an aryl group including, but not limited to, phenoxy, 1-naphthoxy and 2-naphthoxy.

The term "arylalkyl" as used herein refers to an aryl group appended to an alkyl radical including, but not limited to, phenylmethyl (benzyl), 2-phenylethyl, 1-naphthylmethyl, 2-pyridylmethyl and 2-quinolylmethyl.

The term "reduced heteroarylalkyl" as used herein refers to a reduced heteroaryl group appended to an alkyl radical including, but not limited to, dihydrothienylmethyl, tetrahydrothienylmethyl, dihydropyranylmethyl, tetraphydropyranylmethyl, dihydroquinolylethyl and tetrahydroquinolylethyl.

The terms "arylalkoxy" and "arylthioalkoxy" as used herein refer to —$OR_{26}$ and —$SR_{26}$, respectively, wherein $R_{26}$ is an arylalkyl group including, but not limited to, phenylmethoxy (i.e., benzyloxy), 1-phenylethoxy, 2-phenylethoxy, 1-naphthylmethyloxy, 2-naphthylmethyloxy, 2-, 3- or 4-pyridylmethoxy, 2-, 3-, 4-, 5-, 6-, 7-, or 8-quinolylmethoxy, benzylthio, 1-phenylthio, 2-phenylthio, 1-naphthylmethylthio, 2-naphthylmethylthio, and 2-, 3- or 4-pyridylmethylthio.

The term "arylalkenyl" as used herein refers to an aryl group appended to an alkenyl radical including, but not limited to, phenylethenyl, 3-phenylprop-1-enyl, 3-phenylprop-2-enyl, 1-naphthylethenyl and 3-pyrid-3-yl-prop-1-enyl.

The terms "halo" and "halogen" as used herein refer to radicals derived from the elements fluorine, chlorine, bromine, and iodine.

The terms "halosubstituted alkyl" and "haloalkyl" as used herein refer to an alkyl group in which one or more hydrogen atoms are substituted by a halogen and include, but are not limited to, chloromethyl, trifluoromethyl and 2,2,2-trichloroethyl.

The term "pharmaceutically acceptable salt" as used herein refers to a relatively non-toxic, inorganic or organic acid addition salt of the compounds of the invention including, but not limited to, hydrochloride, hydrobromide, sulfate, nitrate, bisulfate. acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactobionate and lauryl sulphate as well as to alkali or alkaline earth salts including, but not limited to, sodium, calcium, potassium and magnesium.

The term "pharmaceutically acceptable cation" refers to non-toxic cations including, but not limited to, those based on the alkali and alkaline earth metals such as sodium, lithium, potassium, magnesium, and the like, as well as nontoxic ammonium, quaternary ammonium and amine cations, including, but not limited to, ammonium, tetramethylammonium, tetraethylammonium, methylamine. dimethylamine, trimethylamine, triethylamine and ethylamine.

The term "ester" as used herein refers to a hydroxyl- or carboxyl-substituted derivative of a compound of the present invention in which the substituting group is a metabolically cleavable group including, but not limited to, glycyl, lysyl, acetyl and succinyl.

The term "prodrug" as used herein refers to a hydroxyl- or carboxyl-substituted derivative of a compound of the present invention in which the substituting group is a metabolically cleavable group including, but not limited to, alkanoyl, aroyl, aminocarbonyl, alkylaminocarbonyl, alkoxycarbonyl and silyl.

The term "residue" as used herein with respect to a non-steroidal antiinflammatory carboxylic acid compound refers to that portion of the antiinflammatory compound which remains after removal of the —COOH portion of the molecule.

Certain compounds of this invention can exist in optically active forms. The R and S isomers and racemic mixtures thereof, as well as mixtures of cis and trans isomers, are contemplated by this invention. Additional assymetric carbon atoms can be present in a substituent group such as an alkyl group. All such isomers as well as the mixtures thereof are intended to be included in the invention.

Method of Treatment

This invention provides a method of treatment of inhibiting 5- and/or 12-lipoxygenase activity in a human or lower mammal host in need of such treatment which method comprises administering to the human or lower mammal host one of the compounds previously described herein in an amount effective to inhibit lipoxygenase activity in the host. The compounds of the present invention may be administered orally, parenterally or topically in dosage unit formulations containing conventional nontoxic pharmaceutically acceptable carriers, adjuvants and vehicles as desired.

The term "parenterally" as used herein includes subcutaneous, intravenous, intraarterial injection or infusion techniques, without limitation. The term "topically" encompasses administration rectally and by inhalation spray, as well as by the more common routes of the skin and the mucous membranes of the mouth and nose.

Total daily dose of the compounds of this invention administered to a host in single or divided doses may be in amounts, for example, of from about 0.001 to about 100 mg/kg body weight daily and more usually 0.01 to 10 mg/kg/day. Dosage unit compositions may contain such amounts of such submultiples thereof as may be used to make up the daily dose. It will be understood, however, that the specific dose level for any particular patient will depend upon a variety of factors including body weight, general health, sex, diet, time and route of administration, rates of absorption and excretion, combination with other drugs and the severity of the particular disease being treated.

Formulation of Pharmaceutical Composition

This invention also provides for compositions in unit dosage form for the inhibition of 5- or 12-lipoxygenase activity in a human or lower mammal host in need of such treatment, comprising a compound of this invention and one or more nontoxic pharmaceutically acceptable carriers, adjuvants or vehicles. The amount of active ingredient that may be combined with such materials to produce a single dosage form will vary depending upon various factors, as indicated above.

A variety of materials can be used as carriers, adjuvants and vehicles in the composition of this invention, as available in the pharmaceutical arts. Injectable preparations, such as oleaginous solutions, suspensions or emulsions, may be formulated according to known art, using suitable dispersing or wetting agents and suspending agents, as needed. The sterile injectable preparation may employ a nontoxic parenterally acceptable diluent or solvent as, for example, sterile nonpyrogenic water or 1,3-butanediol. Among the other acceptable vehicles and solvents that may be employed are 5% dextrose injection, Ringer's injection and isotonic sodium chloride injection (as described in the USP/NF). In addition, sterile, fixed oils are conventionally employed as solvents or suspending media. For this purpose any bland fixed oil may be used, including synthetic mono-, di- or triglycerides. Fatty acids such as oleic acid can also be used in the preparation of injectable compositions.

Suppositories for rectal administration of the compound of this invention can be prepared by mixing the drug with suitable nonirritating excipients such as cocoa butter and polyethylene glycols, which are solid at ordinary temperatures but liquid at body temperature and which therefore melt in the rectum and release the drug.

Solid dosage forms for oral administration include capsules, tablets, pills, troches, lozenges, powders and granules. In such solid dosage forms, the active compound may be admixed with at least one inert diluent such as sucrose, lactose or starch. Such dosage forms may also comprise, as is normal practice, pharmaceutical adjuvant substances. e.g., stearate lubricating agents. In the case of capsules, tablets and pills, the dosage forms may also comprise buffering agents. Solid oral preparations can also be prepared with enteric or other coatings which modulate release of the active ingredients.

Liquid dosage forms for oral administration include pharmaceutically acceptable emulsions, solutions, suspensions, syrups and elixirs containing inert nontoxic diluents commonly used in the art, such as water and alcohol. Such compositions may also comprise adjuvants, such as wetting, emulsifying, suspending, sweetening, flavoring and perfuming agents.

Synthesis of the Compounds

Compounds of this invention can be prepared by the processes presented hereinbelow. In certain cases where the non-steroidal antiinflammatory drug (NSAID) contains functional groups which might interfere with a desired transformation outlined in the following processes, it is recognized that common methods of protection of these groups followed by deprotection at a later stage in the preparation of the desired product can be employed. A general reference source for methods of protection and deprotection is T. W. Greene, "Protective Groups in Organic Synthesis", Wiley-Interscience, New York, 1981.

4-Hydroxythiazoles of Formula I are prepared by the reaction sequence outlined in Scheme I, below. The nonsteroidal antiinflammatory drugs, Z—$CO_2H$, are converted to the corresponding thioamides by a sequence of known methods, for example, by successive treatment with (a) thionyl chloride, (b) ammonium hydroxide, and (c) Lawesson's reagent. The thioamides are then reacted with an alpha haloester or alpha haloacid chloride or alpha haloacid bromide at high temperature in toluene to provide the corresponding 4-hydroxythiazoles.

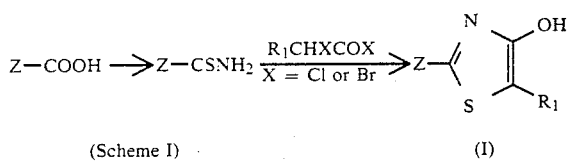

(Scheme I)  (I)

4-Hydroxythiazoles of Formula II are prepared by the reaction sequence outlined in Scheme II. The nonsteroidal antiinflammatory drugs, Z—$CO_2H$, are converted to the corresponding homologous acid Z—$CH_2CO_2H$ by known methods. For example, the following references describe applicable methods: Kowalski, C. J., Hague, M. S., Fields, K. W., J. Am. Chem. Soc., 107:1429 (1985); Johnson, W. S., Christiansen, R. G., Ireland, R. E., J. Am. Chem. Soc., 79:1995 (1957); Dinizo, S. E., Freerksen, R. W., Pabst, W. E., Watt, D. S., J. Am. Chem. Soc., 99:182 (1977). Conversion to the alpha-halo acid halide analog Z—CHX—COX where X=Cl or Br also is accomplished by known methods. Reaction of the alpha-haloacid halide with a thioamide compound provides the desired hydroxythiazole.

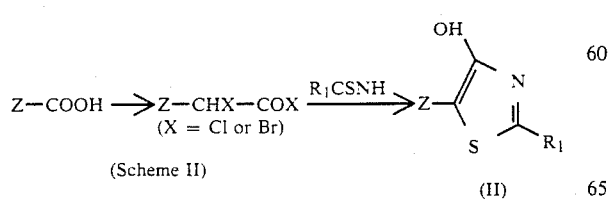

(Scheme II)  (II)

Other known methods to access the intermediate Z—CHX—COX from starting materials other than NSAID carboxylic acids substrates are also taught by Example 5.

The following examples are for the purpose of illustrating the use of the above synthetic schemes to prepare representative compounds of the present invention, and are not intended to limit the scope of the claims in any way.

EXAMPLE 1

2-[1-(6-methoxy-2-naphthyl)ethyl]-5-phenyl-4-hydroxythiazole (Formula I,
Z=1-(6-methoxy-2-naphthyl)ethyl, $R_1$=phenyl, M=H).

Oxalyl chloride (1.9 mL, 22 mmol) was added dropwise to naproxen (5 g, 22 mmol) in methylene chloride (100 mL) at 5° C. under nitrogen, and N,N-Dimethylformamide (0.02 mL) was added to catalyze the reaction. The reaction mixture was allowed to warm to 23° C. and stirred for 8 hours. Concentrated ammonium hydroxide (10 mL) was added to the cooled (5° C.) solution. After 1 hour at 23° C. the reaction mixture was concentrated in vacuo and water (200 mL) was added. The precipitate was collected and recrystallized from methylene chloride/methanol to afford the pure amide (4.2 g, 85%), mp 177°–178° C. $^1$H NMR (60 MHz, DMSO-$d_6$) 1.41 (3H, d, J=7 Hz), 3.65 (1H, g, J=7 Hz), 3.80 (3H, s), 6.72 (2H, br s), 7.1–7.8 (6H, m); MS: 229 (M+).

Anal. Calc'd for $C_{14}H_{15}NO_2$: C,73.36; H, 6.55; N, 6.11.

Found: C,73.69; H,6.58; N, 6.01.

Lawesson's reagent (3.6 g, 9 mmol) was added to the amide (4 g, 18 mmol) suspended in toluene (200 mL) at 23° C. under nitrogen. The reaction mixture was then heated at 100° C. for 2 hours. After cooling to 23° C., the organic solvent was evaporated and the crude residue chromatographed (silica gel, chloroform) to afford the thioamide (1.4 g, 33%).

mp 144°–145° C.; $^1$H NMR (60 MHz, DMSO-$d_6$) 1.55 (3H, d, J=7 Hz), 3.81 (3H, s), 4.11 (1H, g, J=7 Hz), 7.05–7.85 (8H, m); MS: 245 (M+).

Anal. Calc'd for $C_{14}H_{15}NOS$: C, 68.57; H, 6.12; N, 5.71.

Found: C, 68.19; H, 6.12; N, 5.75.

Alpha-Chlorophenylacetylchloride (0.65 mL, 4.1 mmol) was added dropwise to the thioamide (1.0 g, 4 mmol) in toluene (100 mL) containing pyridine (0.65 mL, 8 mmol) under nitrogen. The reaction mixture was then heated at 108° C. for 4 hours. The reaction mixture was cooled and the solvent evaporated. Recrystallization from ether/ethanol provided the title compound (0.3 g, 27%).

mp 245°–246° C.; $^1$H NMR (60 MHz, DMSO-$d_6$): 1.61 (3H, d. J=7 Hz), 3.81 (3H, s), 4.21 (1H, g, J=7 Hz), 7.1–8.0 (11H. m), 10.41 (1H, s); MS: 361 (M+).

Anal. Calc'd for $C_{22}H_{19}NO_2S$: C, 73.13; H, 5.26; N, 3.88.

Found: C, 73.28; H, 5.24; N, 3.92.

EXAMPLE 2

2-[1-(4-isobutylphenyl)ethyl]-5-phenyl-4-hydroxythiazole (Formula I, Z=2-[1-(4-isobutylphenyl)ethyl], $R_1$=phenyl, M=H)

The title compound was prepared according to the method of Example 1 except that ibuprofen was used instead of naproxen.

mp 185°–186° C.; $^1$H NMR (60 MHz, DMSO-d$_6$) 0.85 (6H, d, J=7 Hz), 1.60 (3H, d, J=7 Hz), 1.85 (1H,m), 2.45 (2H, d, J=7 Hz), 4.01 (1H, g, J=7 Hz), 7.0–8.0 (9H,m), 10.27 (1H,s); MS: 337 (M+).

Anal. Calc'd. for C$_{21}$H$_{23}$NOS: C, 74.78; H. 6.82: N, 4.54.

Found: C, 74.39: H, 6.85: N, 4.51.

EXAMPLE 3

2-[(4-isobutylphenyl)methyl]-5-phenyl-4-hydroxythiazole (Formula I, Z=2-[(4-isobutylphenyl)methyl], R$_1$=phenyl, M=H)

The title compound was prepared according to the method of Example 1 except that ibufenac was used instead of naproxen.

mp 196°–197° C.; $^1$H NMR (60 MHz, DMSO-d$_6$) 0.81 (6H, d, J=7 Hz), 1.75 (1H, m), 2.44 (2H, d, J=7 Hz), 3.78 (2H, s), 7.0–8.0 (9H, m), 10.55 (1H,s); MS: 323 (M+)

Anal. Calc'd. for C$_{20}$H$_{21}$NOS: C, 74.30; H, 6.50; N, 4.33.

Found: C, 74,68; H, 6.47; N, 4.37.

EXAMPLE 4

2-[1-(4-isobutylphenyl)propyl]-5-phenyl-4-hydroxythiazole (Formula I, Z=2-[1-(4-isobutylphenyl)propyl], R$_1$=phenyl, M=H)

The title compound was prepared according to the method of Example 1 except that butibufen was used instead of naproxen.

mp 168°–169° C.; $^1$H NMR (60 MHz.DMSO-d$_6$) 0 85 (3H, d, J=7 Hz), 0.91 (3H, t, J=7 Hz), 1.58 (2H, m), 1.85 (1H, m), 2.45 (2H, d, J=7 Hz), 4.02 (1H, t, J=7 Hz), 7.0–8.0 (9H, m), 10.55 (1H, s); MS: 351 (M+).

Anal. Calc'd. for C$_{22}$H$_{25}$NOS: C,75.21; H, 7.12; N, 3.99.

Found: C, 74.98; H, 7.14; N, 4.10.

EXAMPLE 5

5-[1-(6-methoxy-2-naphthyl)ethyl]-2-phenyl-4-hydroxythiazole (Formula II, Z=5-[1-(6-methoxy-2-naphthyl)ethyl], R$_1$=phenyl, M=H)

Methyl diethylphosphonoacetate (1.6 g, 7 5 mmol) and NaH (0.19 g, 7.5 mmol) in THF (25 mL) was added to 2-acetyl-6-methoxynaphthalene (1.5 g, 7.5 mmol) in THF (50 mL) at 23° C. under nitrogen. After refluxing for 20 hours, the reaction mixture was cooled, saturated NH$_4$Cl added, and the mixture poured into water. The solution was extracted with ether and the organic extracts were dried (MgSO$_4$) and the solvent evaporated. Chromatography (silica gel, ether/pentane) afforded methyl 3-(6-methoxy-2-naphthyl)-2-butenoate (0.75 g). This intermediate (0.51 g, 2 mmol) in methanol (50 mL) was hydrogenated with 20% Pd/C (50 mg) at 3 atm at 23° C. until the theoretical amount of hydrogen was taken up. Removal of solvent and catalyst gave the crude ester which was dissolved in isopropanol/water : 2/1 (40 mL). Lithium hydroxide (82 mg, 2 mmol) was added and the reaction mixture stirred at 23° C. for 1 hour. Saturated ammonium chloride was added and the mixture extracted with ethyl acetate. Removal of solvent followed by recrystallization from methanol/water gave 3-(6-methoxy-2-naphthyl) butyric acid (0.45 g). Bromine (3 mL of a 1M solution in CCl$_4$, 3 mmol) was added slowly to the acid (0.37 g, 1.5 mmol) and PBr$_3$ (0.4 g, 1.5 mmol) in CCl$_4$ (20 mL) at 23° C. under nitrogen. The mixture was heated at 80° C. for 20 hours. The mixture was then cooled and poured into ice water. Extraction with benzene followed by drying (Na$_2$SO$_4$) and evaporation gave a crude residue which was distilled under reduced pressure (0.5 mm) to afford 2-bromo-3-(6-methoxy-2-naphthyl)butyrylbromide (0.55 g). $^1$H NMR(60 MHz, DMSO-d6): 1.30 (3H, d J=7 Hz), 3.80 (3H, s), 4.01 (1H, g, J=7 Hz), 4.20 (1H, d, J=7 Hz), 7.0–8.0 ( 6H, m); Mass Spectrum: 386(M+).

Anal. Calc'd for C$_{15}$H$_{14}$Br$_2$O$_2$: C,46.63; H, 3.63.

Found: C, 46.87; H, 3.59.

To a solution of 2-bromo-3-(6-methoxy-2-naphthyl) butyrylbromide (386 mg, 1 mmol) in toluene (20 mL) was added thiobenzamide (137 mg, 1 mmol) and pyridine (0.16 mL, 2 mmol) in toluene (60 mL) at 23° C. The reaction mixture was heated at 100° C. for 4 hours and then cooled and the solvent removed in vacuo. Recrystallization of the residue from ethanol/ether provided the desired product (128 mg). mp 224°–226° C., $^1$H NMR (60 MHz, DMSO-d$_6$) 1.30 (3H, d, J=7 Hz), 3.82 (3H, s), 3.92 (1H, g, J=7 Hz), 7.1–8.0 (11H, m), 10.55 (1H, s); Mass Spectrum: 361 (M+).

Anal Calc'd for C$_{22}$H$_{19}$NO$_2$S: C, 73.12; H, 5.26; N, 3.88.

Found: C, 72.89; H, 5.27; N, 4.01.

EXAMPLE 6

2-[1-(6-methoxy-2-naphthyl)ethyl]-5-(4-methoxyphenyl)-4-hydroxythiazole (Formula I, Z=1-(6-methoxy-2-naphthyl)ethyl, R$_1$=4-methoxyphenyl. M=H)

The desired compound is prepared according to the method of Example 1 except using 2-chloro-2-(4'-methoxyphenyl)acetylchloride instead of alpha-chlorophenylacetylchloride.

EXAMPLE 7

2-[1-(6-methoxy-2-naphthyl)ethyl]-5-(4-carbomethoxyphenyl)-4-hydroxythiazole (Formula I, Z=1-(6-methoxy-2-naphthyl)ethyl, R$_1$=4-carbomethoxyphenyl, M=H).

The desired compound is prepared according to the method of Example 1 except using 2-chloro-2-(4'-carbomethoxyphenyl)acetylchloride instead of alpha-chlorophenylacetylchloride.

EXAMPLE 8

2-[1-(4-isobutylphenyl)propyl]-5-(4-methoxyphenyl)-4-hydroxythiazole (Formula I, Z=2-[1-(4-isobutylphenyl)propyl], R$_1$=4-methoxyphenyl, M=H)

The desired compound is prepared according to the method of Example 4 except using 2-chloro-2-(4'-methoxyphenyl)acetylchloride instead of alpha-chlorophenylacetylchloride.

EXAMPLE 9

2-[1-(4-isobutylphenyl)propyl]-5-(4-methoxycarbonylphenyl)-4-hydroxythiazole (Formula I, Z=2-[1-(4-isobutylphenyl)propyl], R$_1$=4-methoxycarbonylphenyl, M=H).

The desired compound is prepared according to method of Example 4 except using 2-chloro-2-(4'-methoxycarbonylphenyl)acetylchloride instead of alpha-chlorophenylacetylchloride.

EXAMPLE 10

2-[1-(4-isobutylphenyl)propyl]-5-(4-fluorophenyl)-4-hydroxythiazole (Formula I,
Z=2-[1-(4-isobutylphenyl)propyl],
$R_1$=4-fluorophenyl, M=H)

The desired compound is prepared according to the method of Example 4 except using 2-chloro-2-(4'-fluorophenyl)acetylchloride instead of alpha-chlorophenylacetylchloride.

EXAMPLE 11

2-[1-(4-isobutylphenyl)propyl]-5-(2.4-difluorophenyl)-4-hydroxythiazole (Formula I,
Z=2-[1-(4-isobutylphenyl)propyl],
$R_1$=2.4-difluorophenyl, M=H)

The desired compound is prepared according to the method of Example 4 except using 2-chloro-2-(2,4-difluorophenyl)acetylchloride instead of alpha-chlorophenylacetylchloride.

EXAMPLE 12

2-[1-(4-isobutylphenyl)propyl]-5-propyl-4-hydroxythiazole (Formula I, Z=2-[1-(4-isobutylphenyl)propyl],
$R_1$=propyl, M=H)

The desired compound is prepared according to the method of Example 4 except using 2-chloropentanoyl chloride instead of alpha-chlorophenylacetylchloride.

EXAMPLE 13

2-[1-(4-isobutylphenyl)propyl]-5-(1-ethylphenyl)-4-hydroxythiazole (Formula I,
Z=2-[1-(4-isobutylphenyl)propyl], $R_1$=1-ethylphenyl, M=H)

The desired compound is prepared according to the method of Example 4 except using 2-chloro-4-phenyl-butyrylchloride instead of alpha-chlorophenylacetylchloride.

EXAMPLE 14

2-[1-(4-isobutylphenyl)propyl]-5-(1-ethenylphenyl)-4-hydroxythiazole (Formula I,
Z=2-[1-(4-isobutylphenyl)propyl],
$R_1$=1-ethenylphenyl, M=H).

The desired compound is prepared according to the method of Example 4 except using 2-chloro-4-phenyl-but-3-enoylchloride instead of alpha-chlorophenylacetylchloride.

EXAMPLE 15

2-[1-(4-isobutylphenyl)propyl]-5-cyclohexyl-4-hydroxythiazole (Formula I,
Z=2-[1-(4-isobutylphenyl)propyl], $R_1$=cyclohexyl, M=H)

The desired compound is prepared according to the method of Example 4 except using 2-chloro-2-cyclohexyl acetylchloride instead of alpha-chlorophenylacetylchloride.

EXAMPLE 16

2-[1-(4-isobutylphenyl)propyl]-5-cyclopropyl-4-hydroxythiazole (Formula I,
Z=2-[1-(4-isobutylphenyl)propyl], $R_1$=cyclopropyl, M=H)

The desired compound is prepared according to the method of Example 4 except using 2-chloro-2-cyclo-propylacetylchloride instead of alpha-chlorophenylacetylchloride.

EXAMPLE 17

2-[1-(4-isobutylphenyl)propyl]-5(thien-2-yl)-4-hydroxythiazole (Formula I, Z=2-[1-(4-isobutylphenyl)propyl],
$R_1$=thien-2-yl, M=H).

The desired compound is prepared according to the method of Example 4 except using 2-chloro-2-thienylacetylchloride instead of alpha-chlorophenylacetylchloride.

EXAMPLE 18

2-[1-(4-isobutylphenyl)propyl]-5-(methylthien2-yl)-4-hydroxythiazole (Formula I,
Z=2-[1-(4-isobutylphenyl)propyl],
$R_1$=methylthien-2-yl, M=H)

The desired compound is prepared according to the method of Example 4 except using 2-chloro-3-(thien-2-yl)propionylchloride instead of alpha-chlorophenylacetylchloride.

EXAMPLE 19

2-[1-(4-isobutylphenyl)propyl]-5-[3-(ethoxycarbonyl)-propyl]-4-hydroxythiazole (Formula I,
Z=2-[1-(4-isobutylphenyl)propyl],
$R_1$=3-(ethoxycarbonyl)propyl, or —$(CH_2)_3C(O)OEt$,
M=H)

The desired compound is prepared according to the method of Example 4 except using 2-chloro-6-ethoxy-chlorophenylacetylchloride instead of alpha-chlorophenylacetylchloride.

EXAMPLE 20

2-[1-(4-isobutylphenyl)propyl]-5-(4-N-methyl-N-hydroxyamidobutyl)-4-hydroxythiazole (Formula I,
Z=2-[1-(4-isobutylphenyl)propyl],
$R_1$=4-N-methyl-N-hydroxyamidobutyl, M=H)

The desired compound is prepared by treatment of the product of Example 19 with N-methylhydroxylamine hydrochloride.

EXAMPLE 21

2-[1-(4-isobutylphenyl)propyl]-5-(4-hydroxybutyl)-4-hydroxythiazole (Formula I,
Z=2-[1-(4-isobutylphenyl)propyl],
$R_1$=4-hydroxybutyl, M=H)

The desired compound is prepared from the product of Example 19 by reduction with $LiBH_4$.

EXAMPLE 22

2-[1-(4-isobutylphenyl)propyl]-5-(4-phenyl)-4-acetyl-thiazole (Formula I, Z=2-[1-(4-isobutylphenyl)propyl],
$R_1$=4-phenyl, M=$COCH_3$)

The desired compound is prepared by treatment of the product of Example 4 with acetic anhydride and pyridine.

EXAMPLE 23

2-[1-(4-isobutylphenyl)propyl]-5-(4-phenyl)-4-hydroxy-thiazole potassium salt (Formula I, $Z=2$-[1-(4-isobutylphenyl)propyl], $R_1=4$-phenyl, $M=K$).

The desired compound is prepared by treatment of the product of Example 4 with potassium hydroxide.

EXAMPLE 24

2-[1-(4-isobutylphenyl)propyl]-5-(4-phenyl)-4-trimethylsilyloxythiazole (Formula I, $Z=2$-[1-(4-isobutylphenyl)propyl], $R_1=4$-phenyl, $M=Si(CH_3)_3$).

The desired compound is prepared by treatment of the product of Example 4 with trimethylsilylimidazole.

EXAMPLE 25

2-[1-(4-isobutylphenyl)propyl]-5-(4-phenyl)-4-glycinylthiazole (Formula I, $Z=2$-[1-(4-isobutylphenyl)propyl], $R_1=4$-phenyl, $M=COCH_2NH_2$)

The desired compound is prepared by treatment of the product of Example 4 with N-BOC glycine and DCC followed by cleavage of the BOC group by standard methods.

EXAMPLE 26

2-[1-(4-isobutylphenyl)propyl]-5-(4-phenyl)-4-succinylthiazole (Formula I, $Z=2$-[1-(4-isobutylphenyl)propyl], $R_1=4$-phenyl, $M=COCH_2CH_2COOH$)

The desired compound is prepared by treatment of the product of Example 4 with succinyl anhydride.

EXAMPLE 27

2-[1-(4-isobutylphenyl)propyl]-5-(4-phenyl)-4-succinyl-N-methyl-N-hydroxyamidothiazole (Formula I, $Z=2$-[1-(4-isobutylphenyl)propyl], $R_1=4$-phenyl, $M=COCH_2CH_2CON(CH_3)OH$)

The desired compound is prepared by treatment of the product of Example 22 with oxalyl chloride followed by N-methylhydroxylamine.

EXAMPLE 28

5-[1-(6-methoxy-2-naphthyl)ethyl]-2-(4-fluorophenyl-4-hydroxythiazole (Formula II, $Z=5$-[1-(6-methoxy-2-naphthyl)ethyl], $R_1=4$-fluorophenyl, $M=H$).

The desired compound is prepared according to the method of Example 5 using 4-fluorothiobenzamide instead of thiobenzamide.

EXAMPLE 29

5-[1-(6-methoxy-2-naphthyl)ethyl]-2-(2,4-difluorophenyl-4-hydroxythiazole (Formula II, $Z=5$-[1-(6-methoxy-2-naphthyl)ethyl], $R_1=2,4$-difluorophenyl, $M=H$)

The desired compound is prepared according to the method of Example 5 using 2,4-difluorothiobenzamide instead of thiobenzamide.

EXAMPLE 30

5-[1-(6-methoxy-2-naphthyl)ethyl]-2-(4-methoxyphenyl-4-hydroxythiazole (Formula II, $Z=5$-[1-(6-methoxy-2-naphthyl)ethyl], $R_1=4$-methoxyphenyl, $M=H$)

The desired compound is prepared according to the method of Example 5 using 4-methoxythiobenzamide instead of thiobenzamide.

EXAMPLE 31

5-[1-(6-methoxy-2-naphthyl)ethyl]-2-(thien-3-yl)-4-hydroxythiazole (Formula II, $Z=5$-[1-(6-methoxy-2-naphthyl)ethyl], $R_1=$thien-3-yl, $M=H$)

The desired compound is prepared according to the method of Example 5 using 3-thioamidothiophene instead of thiobenzamide.

EXAMPLE 32

5-[1-(6-methoxy-2-naphthyl)ethyl]-2-(4-pyridyl)-4-hydroxythiazole (Formula II, $Z=5$-[1-(6-methoxy-2-naphthyl)ethyl], $R_1=4$-pyridyl, $M=H$)

The desired compound is prepared according to the method of Example 5 using 4-thioamidopyridine instead of thiobenzamide.

EXAMPLE 33

5-[1-(6-methoxy-2-naphthyl)ethyl]-2-(2-pyridyl)-4-hydroxythiazole (Formula II, $Z=5$-[1-(6-methoxy-2-naphthyl)ethyl], $R_1=2$-pyridyl, $M=H$)

The desired compound is prepared according to the method of Example 5 using 2-thioamidopyridine instead of thiobenzamide.

EXAMPLE 34

5-[1-(6-methoxy-2-naphthyl)ethyl]-2-(2-benzothienyl)-4-hydroxythiazole (Formula II, $Z=5$-[1-(6-methoxy-2-naphthyl)ethyl], $R_1=2$-benzothienyl, $M=H$)

The desired compound is prepared according to the method of Example 5 using 2-thioamidobenzothiophene instead of thiobenzamide.

EXAMPLE 35

5-[1-(6-methoxy-2-naphthyl)ethyl]-2-(2-benzothiazoyl)-4-hydroxythiazole (Formula II, $Z=5$-[1-(6-methoxy-2-naphthyl)ethyl], $R_1=2$-benzothiazole, $M=H$)

The desired compound is prepared according to the method of Example 5 using 2-thioamidobenzothiazole instead of thiobenzamide.

EXAMPLE 36

5-[1-(6-methoxy-2-naphthyl)ethyl]-2-(2-thiazoyl)-4-hydroxythiazole (Formula II, $Z=5$-[1-(6-methoxy-2-naphthyl)ethyl], $R_1=2$-thiazole, $M=H$)

The desired compound is prepared according to the method of Example 5 using 2-thioamidothiazole instead of thiobenzamide.

EXAMPLE 37

5-[1-(6-methoxy-2-naphthyl)ethyl]-2-phenyl-4-acetoxythiazole (Formula II,
Z=5-[1-(6-methoxy-2-naphthyl)ethyl], $R_1$=phenyl, M=COCH$_3$)

The desired compound is prepared by treatment of the product of Example 5 with acetic anhydride and pyridine.

EXAMPLE 38

5-[1-(6-methoxy-2-naphthyl)ethyl]-2-phenyl-4-hydroxythiazole potassium salt (Formula II,
Z=5-[1-(6-methoxy-2-naphthyl)ethyl], $R_1$=phenyl, M=COCH$_3$)

The desired compound is prepared by treatment of the product of Example 5 with potassium hydroxide.

EXAMPLE 39

5-[1-(6-methoxy-2-naphthyl)ethyl]-2-phenyl-4-methoxycarbonyloxythiazole (Formula II,
Z=5-[1-(6-methoxy-2-naphthyl)ethyl], $R_1$=phenyl, M=COOCH$_3$)

The desired compound is prepared by treatment of the product of Example 5 with chloromethylformate and pyridine.

EXAMPLE 40

5-[1-(6-methoxy-2-naphthyl)ethyl]-2-phenyl-4-N-methyl-N-hydroxycarbonyl-oxythiazole (Formula II,
Z=5-[1-(6-methoxy-2-naphthyl)ethyl], $R_1$=phenyl, M=CON(CH$_3$)OH The desired compound is prepared by treatment of the product of Example 5 with phosgene and N-methylhydroxylamine.

EXAMPLE 41

5-[1-(6-methoxy-2-naphthyl)ethyl]-2-phenyl-4-succinylthiazole (Formula II,
Z=5-[1-(6-methoxy-2-naphthyl)ethyl], $R_1$=phenyl, M=COCH$_2$CH$_2$COOH)

The desired compound is prepared by treatment of the product of Example 5 with succinic anhydride.

EXAMPLE 42

5-[1-(6-methoxy-2-naphthyl)ethyl]-2-[1-(4-isobutylphenyl)ethyl]-4-acetoxythiazole (Formula II,
Z=5-[1-(6-methoxy-2-naphthyl)ethyl],
$R_1$=[1-(4-isobutylphenyl)ethyl], M=COCH$_3$)

The desired compound is prepared according to the method of Example 5 using thioamidoibuprofen instead of thiobenzamide.

EXAMPLE 43

5-[1-(6-methoxy-2-naphthyl)ethyl]-2-[1-(4-isobutylphenyl)propyl]-4-hydroxythiazole (Formula II,
Z=5-[1-(6-methoxy-2-naphthyl)ethyl],
$R_1$=[1-(4-isobutylphenyl)propyl], M=H)

The desired compound is prepared according to the method of Example 5 using thioamidobutibufen instead of thiobenzamide.

EXAMPLE 44

2-[1-(4-isobutylphenyl)ethyl]-5-[1-(4isobutylphenyl)ethyl]-4-hydroxythiazole (Formula II,
Z=5-[1-(4-isobutylphenyl)ethyl],
$R_1$=[1-(4-isobutylphenyl)ethyl], M=H)

The desired compound is prepared according to the method of Scheme II using ibuprofen and thioamidoibuprofen.

EXAMPLE 45

2-[1-(6-methoxy-2-naphthyl)ethyl]-5-[1-(4-isobutylphenyl)ethyl]-4-hydroxythiazole (Formula I,
Z=2-[1-(6-methoxy-2-naphthyl)ethyl],
$R_1$=[1-(4-isobutylphenyl)ethyl], M=H)

The desired compound is prepared according to the method of Scheme II using naproxen and thioamidoibuprofen.

EXAMPLE 46

2-[1-(6-methoxy-2-naphthyl)ethyl]-5-[1-(4-isobutylphenyl)ethyl]-4-benzoylthiazole (Formula I,
Z=2-[1-(6-methoxy-2-naphthyl)ethyl],
$R_1$=[1-(4-isobutylphenyl)ethyl], M=COC$_6$H$_5$)

The desired compound is prepared by treatment of the product of example 45 with benzoyl chloride and pyridine.

EXAMPLE 47

2-[1-(4-phenoxyphenyl)ethyl]-5-phenyl-4-hydroxythiazole (Formula I, Z=2-[1-(4-phenoxyphenyl)ethyl],
$R_1$=phenyl, M=H)

The desired compound is prepared according to the method of Example 1 using fenoprofen instead of naproxen.

EXAMPLE 48

2-[1-(2-(4-chlorophenyl)benzoxaz-5-yl)ethyl]-5-phenyl-4-hydroxythiazole (Formula I,
Z=2-[1-(2-(4-chlorophenyl)benzoxaz-5-yl)ethyl],
$R_1$=phenyl, M=H).

The desired compound is prepared according to the method of Example 1 using benoxaprofen instead of naproxen.

EXAMPLE 49

2-[2-(4,5-diphenyloxaz-2-yl)ethyl]-5-phenyl-4-hydroxythiazole (Formula I,
Z=2-[2-(4,5-diphenyloxaz-2-yl)ethyl], $R_1$=phenyl, M=H)

The desired compound is prepared according to the method of Example 1 using oxaprozin instead of naproxen.

EXAMPLE 50

2-[2-(N-methyl-9-methoxyphenothiazin-4-yl)ethyl]-5-phenyl-4-hydroxythiazole (Formula I,
Z=2-[2-(N-methyl-9-methoxyphenothiazin-4-yl)ethyl],
$R_1$=phenyl, M=H).

The desired compound is prepared according to the method of Example 1 using protizinic acid instead of naproxen.

EXAMPLE 51

2-[5-fluoro-2-methyl-(4-methylsulfinylbenzylidene)-inden-3-ylmethyl]-5-phenyl-4-hydroxythiazole (Formula I, Z=2-[5-fluoro-2-methyl-(4-methylsulfinyl benzylidene)-inden-3-ylmethyl], $R_1$=phenyl, M=H)

The desired compound is prepared according to the method of Example 1 using sulindac instead of naproxen.

Inhibition of 5-Lipoxygenase

Inhibition of 5-lipoxygenase activity was determined using the 20,000x g supernatant from homogenized RBL-1 cells in a similar manner as that described by Dyer and coworkers (Dyer, R. D.; Haviv, F.; Hanel, A. M.; Bornemier, D. A.; Carter, G. W. *Fed. Proc., Fed. Am. Soc. Exp. Biol.*, 43:1462A, (1984).) $IC_{50}$ values (concentration of compound producing 50% enzyme inhibition) were calculated by linear regression analysis of percentage inhibition versus log inhibitor concentration plots.

| EXAMPLE | $IC_{50}$ ($10^{-6}$M) | 95% Confidence Limits ($10^{-6}$M) |
|---------|------------------------|-------------------------------------|
| 1 | 0.42 | 0.36–0.47 |
| 2 | 0.71 | 0.68–0.74 |
| 3 | 1.1 | 1.0–1.2 |
| 4 | 0.06 | 0.05–0.07 |
| 5 | 0.9 | 0.6–1.2 |

What is claimed is:
1. A compound of the formula

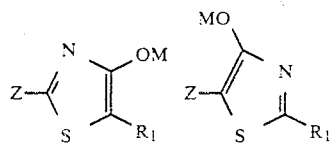

wherein $R_1$ is selected from the group consisting of
(a) alkyl of from one to six carbon atoms;
(b) alkenyl of from two to six carbon atoms;
(c) cycloalkyl of from three to eight carbon atoms;
(d) aryl, selected from the group consisting of
  phenyl,
  1- and 2-naphthyl,
  thienyl,
  furanyl,
  thiazolyl,
  pyridyl,
  pyrimidyl,
  oxazolyl,
  benzothienyl,
  benzofuranyl,
  benzothiazolyl,
  indolyl,
  quinolyl, and
  isoquinolyl,
(e) arylalkyl wherein the aryl portion is as defined above and the alkyl portion is of from one to six carbon atoms;
(f) arylalkenyl wherein the aryl portion is as defined above and the alkenyl portion is of from two to six carbon atoms;
(g) reduced heteroaryl selected from the group consisting of
  dihydrothienyl,
  tetrahydrothienyl,
  dihydrofuranyl,
  tetrahydrofuranyl,
  dihydropyridyl,
  tetrahydropyradyl,
  dihydroquinolyl,
  tetrahydroquinolyl,
  dihydroindolyl, and
(h) reduced heteroarylalkyl in which the reduced heteroaryl portion is as defined above, and the alkyl portion is of from one to six carbon atoms; and any of (a) through (h) above substituted by
  halogen,
  alkyl of from one to six carbon atoms,
  halosubstituted alkyl of from one to six carbon atoms,
  aryl as defined above,
  arylalkyl as defined above,
  reduced heteroaryl as defined above,
  arylalkoxy wherein the aryl portion is as defined above and the alkoxy portion is of from one to six carbon atoms,
  cyano,
  nitro,
  —C(O)R$_4$,
  —SO$_2$R$_4$,
  —NR$_5$R$_6$,
  —OR$_6$,
  —C(O)CX$_1$X$_2$NR$_6$R$_7$,
  —C(O)N(OH)R$_6$,
  —NR$_6$C(O)R$_4$,
  —CR$_5$(NH$_2$)CO$_2$R$_5$,
  —NHCX$_1$X$_{2CO2}$R$_5$,
  —C(NOH)NHOH, and
  —C(O)NHNR$_5$R$_6$;
  wherein
  R$_4$ is selected from
    hydrogen,
    alkyl of from one to six carbon atoms,
    alkenyl of from two to six carbon atoms,
    cycloalkyl of from three to eight carbon atoms,
    cycloalkenyl of from three to eight carbon atoms,
    aryl as defined above,
    arylalkyl as defined above,
    reduced heteroaryl as defined above,
    reduced heteroarylalkyl as defined above,
    —OR$_5$,
    —NHCX$_1$X$_2$CO$_2$R$_5$, and
    —NR$_6$R$_7$;
  R$_5$ is selected from
    hydrogen,
    alkyl of from one to six carbon atoms,
    alkenyl of from two to six carbon atoms,
    cycloalkyl of from three to eight carbon atoms,
    aryl as defined above,
    arylalkyl as defined above,
    reduced heteroaryl as defined above, and
    reduced heteroarylalkyl as defined above.
  R$_6$ and R$_7$ are independently selected from
    hydrogen,
    alkyl of from one to six carbon atoms,
    alkenyl of from two to six carbon atoms,
    cycloalkyl of from three to eight carbon atoms, aryl as defined above,
arylalkyl as defined above,
reduced heteroaryl as defined above, and
—(CH$_2$)$_n$OR$_5$ wherein n is 2 to 4;

X$_1$ and X$_2$ are independently selected from
hydrogen,
alkyl of from one to six carbon atoms,
alkenyl of from two to six carbon atoms,
cycloalkyl of from three to eight carbon atoms,
aryl as defined above, and
arylalkyl as defined above;

M is selected from
hydrogen,
a pharmaceutically acceptable cation,
—COR$_4$,
—C(O)CX$_1$X$_2$NR$_6$R$_7$,
—CR$_8$R$_9$R$_{10}$,
—CR$_2$CR$_8$(OR$_{10}$)CH$_2$OR$_{11}$, and
—SiR$_{12}$R$_{13}$R$_{14}$;

R$_8$, R$_9$, R$_{10}$ and R$_{11}$ are independently selected from
hydrogen,
alkyl of from one to six carbon atoms,
aryl as defined above,
arylalkyl as defined above,
—(CH$_2$)$_n$OR$_5$ wherein n is 2 to 4, or
at least two of R$_8$, R$_9$, R$_{10}$ and R$_{11}$ together form a ring system containing 5 to 10 atoms;

R$_{12}$, R$_{13}$ and R$_{14}$ are independently selected from
alkyl of from one to six carbon atoms, and
aryl as defined above; and Z is the residue of a non-steroidal antiinflammatory drug having the structure Z—COOH and selected from the group consisting of benoxaprofen, benzofenac, bucloxic acid, butibufen, carprofen, cicloprofen, cinmetacin, clidanac, clopirac, diclofenac, etodolac, fenbufen, fenclofenac, fenclorac, fenoprofen, fentiazac, fluoxaprofen, fluraprofen, furobufen, furofenac, ibuprofen, ibufenac, indomethacin, indoprofen, isoxepac, ketoprofen, lonazolac, metiazinic, miroprofen, naproxen, oxaprozin, oxepinac, pirprofen, pirazolac, protizinic acid, sulindac, tiaprofenic acid, tolmetin, and zomepirac; or a pharmaceutically acceptable salt, ester, or pro-drug thereof.

2. The compound according to claim 1, wherein R$_1$ is selected from propyl, cyclopropyl, cyclohexyl, phenyl, 4-phenyl, 4-fluorophenyl, 2,4-difluorophenyl, 1-ethylphenyl, 4-methoxyphenyl, 4-carbomethoxyphenyl, 4-methoxycarbonylphenyl, thien-2-yl, thien-3-yl, methylthien-2yl, 2-benzothienyl, 2-thiazole, 2-benzothiazole, 2-pyridyl, 4-pyridyl, 4-hydroxybutyl, 4-N-methyl-N-hydroxyamidobutyl, 3-(ethoxycarbonyl)propyl, 1-(4-isobutylphenyl)ethyl and 1-(4-phenoxyphenyl)ethyl.

3. The compound according to claim 1 wherein Z is selected from benoxaprofen, benzofenac, bucloxic acid, butibufen, carprofen, cicloprofen, cinmetacin, clidanac, clopirac, diclofenac, etodolac, fenbufen, fenclofenac, fenclorac, fenoprofen, fentiazac, flunoxaprofen, furaprofen, furobufen, furofenac, ibuprofen, ibufenac, indomethacin, indoprofen, isoxepac, ketoprofen, lonazolac, metiazinic, miroprofen, naproxen, oxaprozin, oxepinac, pirprofen, pirazolac, protizinic acid, sulindac, suprofen, tiaprofenic acid, tolmetin, and zomepirac.

4. The compound according to claim 1 wherein R$_1$ is phenyl and M is hydrogen.

5. A compound selected from the following:

2-[1-(6-methoxy-2-naphthyl)ethyl]-5-phenyl-4-hydroxythiazole;
2-[1-(4-isobutylphenyl)ethyl]-5-phenyl-4-hydroxythiazole;
2-[(4-isobutylphenyl)methyl]-5-phenyl-4-hydroxythiazole;
2-[1-(4-isobutylphenyl)propyl]-5-phenyl-4-hydroxythiazole;
5-[1-(6-methoxy-2-naphthyl)ethyl]-2-phenyl-4-hydroxythiazole;
2-[1-(6-methoxy-2-naphthyl)ethyl]-5-(4-methoxyphenyl)-4-hydroxythiazole;
2-[1-(6-methoxy 2-naphthyl)ethyl]-5-(4-carbomethoxyphenyl)-4-hydroxythiazole;
2-[1-(4-isobutylphenyl)propyl]-5-(4-methoxyphenyl)-4-hydroxythiazole;
2-[1-(4-isobutylphenyl)propyl]-5-(4-methoxycarbonylphenyl)-4-hydroxythiazole;
2-[1-(4-isobutylphenyl)propyl]-5-(4-fluorophenyl)-4-hydroxythiazole;
2-[1-(4-isobutylphenyl)propyl]-5-(2,4-difluorophenyl)-4-hydroxythiazole;
2-[1-(4-isobutylphenyl)propyl]-5-(propyl)-4-hydroxythiazole;
2-[1-(4-isobutylphenyl)propyl]-5-(1-ethylphenyl)-4-hydroxythiazole;
2-[1-(4-isobutylphenyl)propyl]-5-(1-ethenylphenyl)-4-hydroxythiazole;
2-[1-(4-isobutylphenyl)propyl]-5-cyclohexyl-4-hydroxythiazole;
2-[1-(4-isobutylphenyl)propyl]-5-cyclopropyl-4-hydroxythiazole;
2-[1-(4-isobutylphenyl)propyl]-5-(thien-2-yl)-4-hydroxythiazole;
2-[1-(4-isobutylphenyl)propyl]-5-(methylthien-2-yl)-4-hydroxythiazole;
2-[1-(4-isobutylphenyl)propyl]-5-[3-(ethoxycarbonyl)propyl]-4-hydroxythiazole;
2-[1-(4-isobutylphenyl)propyl]-5-(4-N-methyl-N-hydroxyamidobutyl)-4-hydroxythiazole;
2-[1-(4-isobutylphenyl)propyl]-5-(4-hydroxybutyl)-4-hydroxythiazole;
2-[1-(4-isobutylphenyl)propyl]-5-(4-phenyl)-4-acetylthiazole;
2-[1-(4-isobutylphenyl)propyl]-5-(4-phenyl)-4-hydroxythiazole potassium salt;
2-[1-(4-isobutylphenyl)propyl]-5-(4-phenyl)-4-trimethylsilyloxythiazole;
2-[1-(4-isobutylphenyl)propyl]-5-(4-phenyl)-4-glycinylthiazole;
2-[1-(4-isobutylphenyl)propyl]-5-(4-phenyl)-4-succinylthiazole;
2-[1-(4-isobutylphenyl)propyl]-5-(4-phenyl)-4-succinyl-N-methyl-N-hydroxyamidothiazole;
5-[1-(6-methoxy-2-naphthyl)ethyl]-2-(4-fluorophenyl-4-hydroxythiazole;
5-[1-(6-methoxy-2-naphthyl)ethyl]-2-(2,4-difluorophenyl-4-hydroxythiazole;
5-[1-(6-methoxy-2-naphthyl)ethyl]-2-(4-methoxyphenyl-4-hydroxythiazole;
5-[1-(6-methoxy-2-naphthyl)ethyl]-2-(thien-3-yl)-4-hydroxythiazole;
5-[1-(6-methoxy-2-naphthyl)ethyl]-2-(4-pyridyl)-4-hydroxythiazole;
5-[1-(6-methoxy-2-naphthyl)ethyl]-2-(2-pyridyl)-4-hydroxythiazole;
5-[1-(6-methoxy-2-naphthyl)ethyl]-2-(2-benzothienyl)-4-hydroxythiazole;

5-[1-(6-methoxy-2-naphthyl)ethyl]-2-(2-benzothiazoyl)-4-hydroxythiazole;

5-[1-(6-methoxy-2-naphthyl)ethyl]-2-(2-thiazoyl)-4-hydroxythiazole;

5-[1-(6-methoxy-2-naphthyl)ethyl]-2-phenyl-4-acetoxythiazole;

5-[1-(6-methoxy-2-naphthyl)ethyl]-2-phenyl-4-hydroxythiazole potassium salt;

5-[1-(6-methoxy-2-naphthyl)ethyl]-2-phenyl-4-methoxycarbonyloxythiazole;

5-[1-(6-methoxy-2-naphthyl)ethyl]-2-phenyl-4-N-methyl-N-hydroxycarbonyl-oxythiazole;

5-[1-(6-methoxy-2-naphthyl)ethyl]-2-phenyl-4-succinylthiazole;

5-[1-(6-methoxy-2-naphthyl)ethyl]-2-[1-(4-isobutylphenyl)ethyl]-4-acetoxythiazole;

5-[1-(6-methoxy-2-naphthyl)ethyl]-2-[1-(4-isobutylphenyl)propyl]-4-hydroxythiazole;

2-[1-(4-isobutylphenyl)ethyl]-5-[1-(4-isobutylphenyl)ethyl]-4-hydroxythiazole;

2-[1-(6-methoxy-2-naphthyl)ethyl]-5-[1-(4-isobutylphenyl)ethyl]-4-hydroxythiazole;

2-[1-(6-methoxy-2-naphthyl)ethyl]-5-[1-(4-isobutylphenyl)ethyl]-4-benzoylthiazole;

2-[1-(4-phenoxyphenyl)ethyl]-5-phenyl-4-hydroxythiazole];

2-[1-(2-(4-chlorophenyl)benzoxaz-5-yl)ethyl]-5-phenyl-4-hydroxythiazole;

2-[2-(4,5-diphenyloxaz-2-yl)ethyl]-5-phenyl-4-hydroxythiazole;

2-[2-(N-methyl-9-methoxyphenothiazin-4-yl)ethyl]-5-phenyl-4-hydroxythiazole;

2-[5-fluoro-2-methyl-(4-methylsulfinylbenzylidene)-inden-3-ylmethyl]-5-phenyl-4-hydroxythiazole; or a pharmaceutically acceptable salt, ester, or pro-drug thereof.

6. A compound selected from the following:

2-[1-(6-methoxy-2-naphthyl)ethyl]-5-phenyl-4-hydroxythiazole;

2-[1-(4-isobutylphenyl)ethyl]-5-phenyl-4-hydroxythiazole;

2-[(4-isobutylphenyl)methyl]-5-phenyl-4-hydroxythiazole;

2-[1-(4-isobutylphenyl)propyl]-5-phenyl-4-hydroxythiazole;

5-[1-(6-methoxy-2-naphthyl)ethyl]-2-phenyl-4-hydroxythiazole; and or a pharmaceutically acceptable salt, ester, or pro-drug thereof.

7. A pharmaceutical composition for inhibiting lipoxygenase enzymes in a mammal in need of such treatment comprising a pharmaceutically acceptable carrier and a therapeutically effective amount of a compound according to claim 1.

8. A method of inhibiting lipoxygenase enzymes in a mammal in need of such treatment comprising administering to such mammal a therapeutically effective amount of a compound according to claim 1.

* * * * *

UNITED STATES PATENT AND TRADEMARK OFFICE
CERTIFICATE OF CORRECTION

PATENT NO. : 5,032,588

DATED : July 16, 1991

INVENTOR(S) : Dee W. Brooks; Francis A. J. Kerdesky

It is certified that error appears in the above-identified patent and that said Letters Patent is hereby corrected as shown below:

Column 23, Line 39:  Replace "furo-" with --fura- --.

Column 23, Line 52:  Replace "thien-2yl," with --thien-2-yl,--.

Column 26, Line 19:  Delete the word "and".

Signed and Sealed this

Fourteenth Day of September, 1993

Attest:

BRUCE LEHMAN

*Attesting Officer*        *Commissioner of Patents and Trademarks*